United States Patent
Paterson et al.

(10) Patent No.: US 10,646,216 B2
(45) Date of Patent: May 12, 2020

(54) KNOTLESS SURGICAL TECHNIQUE

(71) Applicant: ARTHREX, INC., Naples, FL (US)

(72) Inventors: John David Paterson, Naples, FL (US); Andrew Christian Petry, Naples, FL (US); Alexander Emmanuel Rodriguez, Weston, FL (US); Patrick Joel Denard, Jacksonville, OR (US)

(73) Assignee: ARTHREX, INC., Naples, FL (US)

( * ) Notice: Subject to any disclaimer, the term of this patent is extended or adjusted under 35 U.S.C. 154(b) by 242 days.

(21) Appl. No.: 15/712,553

(22) Filed: Sep. 22, 2017

(65) Prior Publication Data

US 2019/0090866 A1 Mar. 28, 2019

(51) Int. Cl.
*A61B 17/04* (2006.01)
*A61F 2/08* (2006.01)

(52) U.S. Cl.
CPC ........ *A61B 17/0401* (2013.01); *A61F 2/0811* (2013.01); *A61B 2017/0404* (2013.01); *A61B 2017/0409* (2013.01); *A61B 2017/0448* (2013.01); *A61B 2017/0477* (2013.01); *A61F 2002/0852* (2013.01); *A61F 2002/0882* (2013.01)

(58) Field of Classification Search
CPC ................ A61B 17/0401; A61B 17/16; A61B 2017/0404; A61B 2017/0409; A61B 2017/0448; A61B 2017/0477; A61F 2002/0852; A61F 2002/0882; A61F 2/0811
See application file for complete search history.

(56) References Cited

U.S. PATENT DOCUMENTS

| | | | |
|---|---|---|---|
| 5,699,657 A | 12/1997 | Paulson | |
| 6,511,498 B1 | 1/2003 | Fumex | |
| 6,517,578 B2 | 2/2003 | Hein | |
| 7,569,059 B2 | 8/2009 | Cerundolo | |
| 7,585,311 B2 | 9/2009 | Green et al. | |
| 7,905,903 B2 | 3/2011 | Stone et al. | |
| 9,179,907 B2 | 11/2015 | ElAttrache et al. | |
| 2008/0188936 A1 | 8/2008 | Ball et al. | |
| 2011/0087280 A1* | 4/2011 | Albertorio | A61B 17/0401 606/232 |
| 2011/0270280 A1 | 11/2011 | Saliman | |
| 2012/0059417 A1 | 3/2012 | Norton et al. | |
| 2014/0249579 A1* | 9/2014 | Heaven | A61B 17/0401 606/232 |
| 2015/0164497 A1 | 6/2015 | Callison et al. | |

* cited by examiner

*Primary Examiner* — Elizabeth Houston
*Assistant Examiner* — Mohamed G Gabr
(74) *Attorney, Agent, or Firm* — Carlson, Gaskey & Olds

(57) ABSTRACT

An illustrative example surgical method includes establishing a tunnel in a bone. At least a portion of the suture is passed through the tunnel. The suture has two ends and first and second loops between the two ends. The first loop includes a button on the suture. The second loop is on one side of the tunnel and the button is on the other side of the tunnel after the portion of the suture has been passed through the tunnel. At least some of the second loop of the suture is passed through soft tissue. Manipulating the second loop over the button positions a portion of the soft tissue between the second loop of the suture and the bone. Adjusting a length of the second loop urges the portion of the soft tissue against the bone where the portion of the soft tissue is held by the suture without tying any knots in the suture.

14 Claims, 8 Drawing Sheets

KNOTLESS SURGICAL TECHNIQUE

BACKGROUND

There are a variety of surgical procedures that involve repairing or replacing soft tissue, such as tendons or ligaments. Soft tissue injuries may leave an individual with joint weakness or limited mobility. In some instances, surgery facilitates soft tissue reattachment to bone for proper joint function.

There are a variety of surgical devices and techniques that facilitate soft tissue repair and healing. With advances in medicine, doctors and medical device suppliers have sought to improve patient outcomes in various ways. One aspect of this pursuit has led to knotless surgical techniques in which suture is used to hold soft tissue in a proper anatomical position to promote healing and reattachment of the soft tissue to bone. Some challenges associated with known knotless devices and techniques include the relatively limited space available on some bones to make the necessary attachment. Additionally, bone tissue varies widely among individuals so surgeons are often presented with relatively weak or inferior bone when trying to secure tissue in place to promote healing.

It would be useful if additional techniques were available to provide, for example, a more predictable bone strength to support the surgical repair.

SUMMARY

An illustrative example surgical method includes establishing a tunnel in a bone. At least a portion of the suture is passed through the tunnel. The suture has two ends and first and second loops between the two ends. The first loop includes a button on the suture. The second loop is on one side of the tunnel and the button is on the other side of the tunnel after the portion of the suture has been passed through the tunnel. At least some of the second loop of the suture is passed through soft tissue. Manipulating the second loop over the button positions a portion of the soft tissue between the second loop of the suture and the bone. Adjusting a length of the second loop urges the portion of the soft tissue against the bone where the portion of the soft tissue is held by the suture without tying any knots in the suture.

An illustrative example surgical kit for performing a surgery to position soft tissue against bone includes a first button, a first suture, a second suture, a second button, a third suture, and a fourth suture. The first suture includes two first suture ends and a first and second loop between the two first suture ends. At least one first securing member on the first suture defines one end of the first and second loops of the first suture, respectively. The first securing member establishes a fixed length of at least the second loop of the first suture without tying a knot in the first suture. The first loop of the first suture includes the first button on the first suture. The second suture includes two second suture ends and a first and second loop between the second suture ends. At least one second securing member is on the second suture. That securing member defines one end of the first and second loops of the second suture, respectively. The second securing member establishes a fixed length of at least the second loop of the second suture without tying a knot in the second suture. The first loop of the second suture includes the first button on the second suture. The third suture includes two third suture ends and first and second loops between the third suture ends. At least one third securing member on the third suture defines one end of the first and second loops of the third suture, respectively. The third securing member establishes a fixed length of at least the second loop of the third suture without tying a knot in the third suture. The fourth suture includes two fourth suture ends and first and second loops between those suture ends. At least one fourth securing member defines one end of the first and second loops of the fourth suture, respectively. The fourth securing member establishes a fixed length of at least a second loop of the fourth suture without tying a knot in the fourth suture. The first loop of the fourth suture includes the second button on the fourth suture.

Various features and advantages of at least one disclosed example embodiment will become apparent to those skilled in the art from the following detailed description. The drawings that accompany the detailed description can be briefly described as follows.

DETAILED DESCRIPTION

Figure 1:
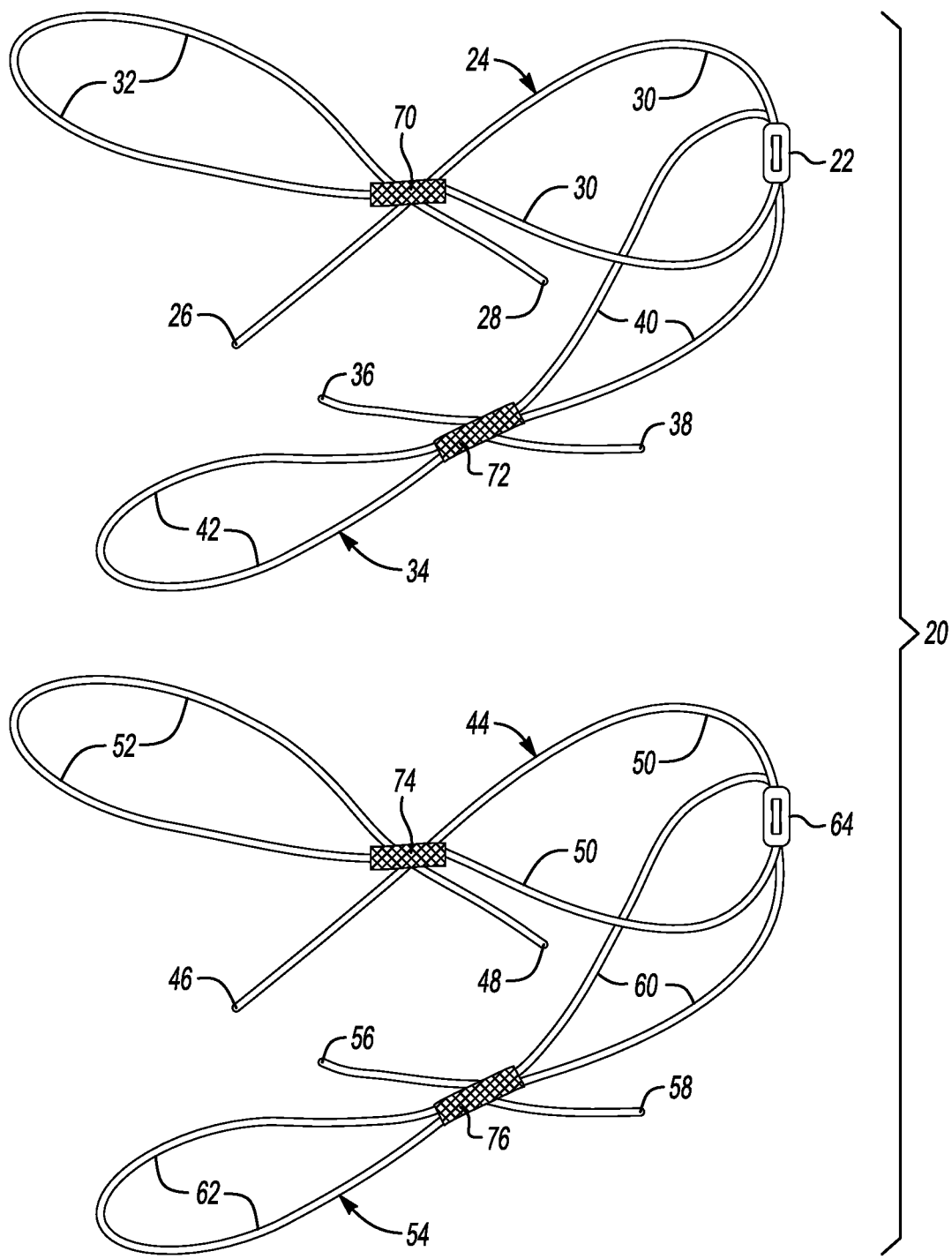
FIG. 1 diagrammatically illustrates an example surgical kit designed according to an embodiment of this invention.

FIG. 1 illustrates a surgical kit 20 that is useful for various surgical techniques including soft tissue repair in which soft tissue is held against bone to facilitate healing and reattachment of the soft tissue to the bone. The example surgical kit 20 allows a surgeon to perform a soft tissue repair without having to tie any knots in the suture used for that repair.

The example surgical kit 20 includes a first button 22. A first suture 24 has ends 26 and 28. The first suture 24 has a first loop 30 and a second loop 32 between the ends 26 and 28. A second suture 34 has ends 36 and 38. The second suture 34 includes a first loop 40 and a second loop 42 between the ends 36 and 38. The first button 22 is on the first loop 30 of the first suture 24 and the first loop 40 of the second suture 34. In other words, a portion of the first suture 24 and a portion of the second suture 34 are each threaded through the first button 22.

The example kit 20 includes a third suture 44 having ends 46 and 48. The third suture 44 includes a first loop 50 and a second loop 52 between the ends 46 and 48. A fourth suture 54 includes ends 56 and 58. The fourth suture 54 includes a first loop 60 and a second loop 62 between the ends 56 and 58. The surgical kit 20 includes a second button 64 on the first loop 50 of the third suture 44 and the first loop 60 of the fourth suture 54.

In the illustrated example embodiment, the surgical kit 20 includes securing members 70, 72, 74 and 76, respectively, on the first suture 24, second suture 34, third suture 44 and fourth suture 54. The securing members 70-76 in this example comprise braided material. In some examples, the braided material is the same material used for the sutures. Various braid configurations are known for use with sutures and those skilled in the art who have the benefit of this description will be able to select appropriate suture and securing member or braid material to meet the needs of their particular situation.

In the illustrated example, the ends of each suture are threaded through the securing member associated with that suture. The securing member defines an end of each loop of the corresponding suture. The ends of the suture threaded through the securing member pass through the securing member in a way that allows for adjusting a length of the corresponding loop by pulling on an end and moving it relative to the securing member.

Figure 2:
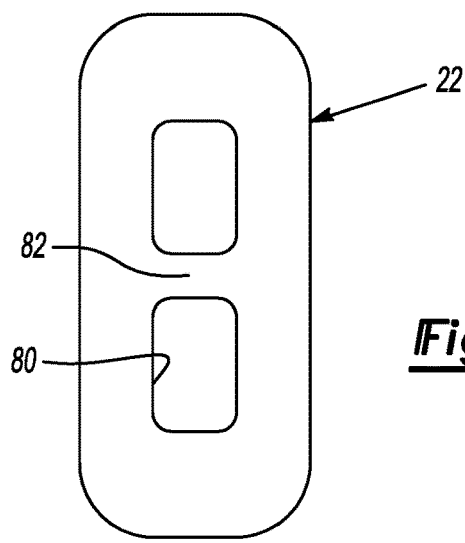
FIG. 2 illustrates selected features of a button that is useful in a surgical kit designed according to an embodiment of this invention.

FIG. 2 illustrates an example configuration of the first button 22. A body of the button has a length-to-width aspect ratio that is greater than one. In this example, the first button 22 has a generally cylindrical shape. The first button 22 includes a hole 80 with a post or support 82 across the hole 80. The sutures, such as the first suture 24 and second suture 34, are threaded through the hole 80 and received about the support 82. Although not specifically illustrated, the second button 64 in most embodiments will be configured the same as the first button 22.

The example surgical kit 20 is useful for soft tissue repair surgical techniques, such as those that involve positioning and securing soft tissue in an anatomical position to facilitate healing and reattachment of the soft tissue to bone. For discussion purposes, a surgical technique involving reattachment of a subscapularis tendon to a humerus bone will be discussed. The surgical kit 20 and the technique described below may be used for repairing other types of soft tissue and may involve other bones.

Figure 3:
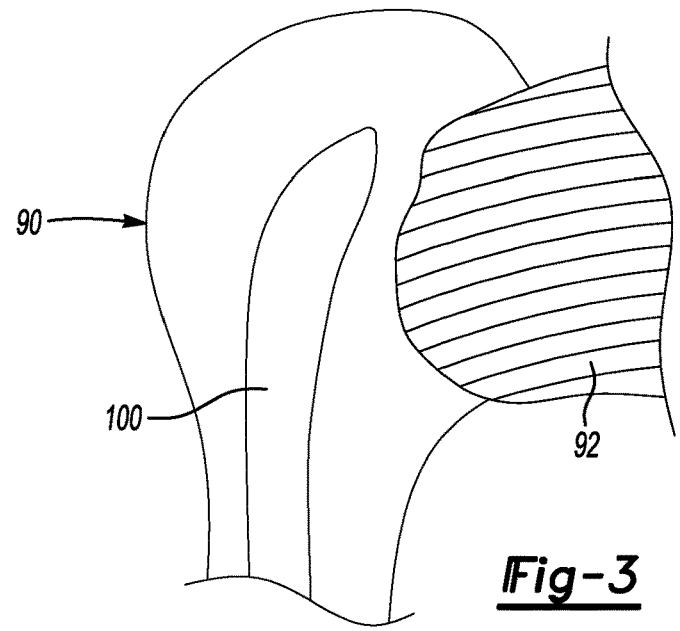
FIG. 3 diagrammatically illustrates an example bone.
Figure 4:
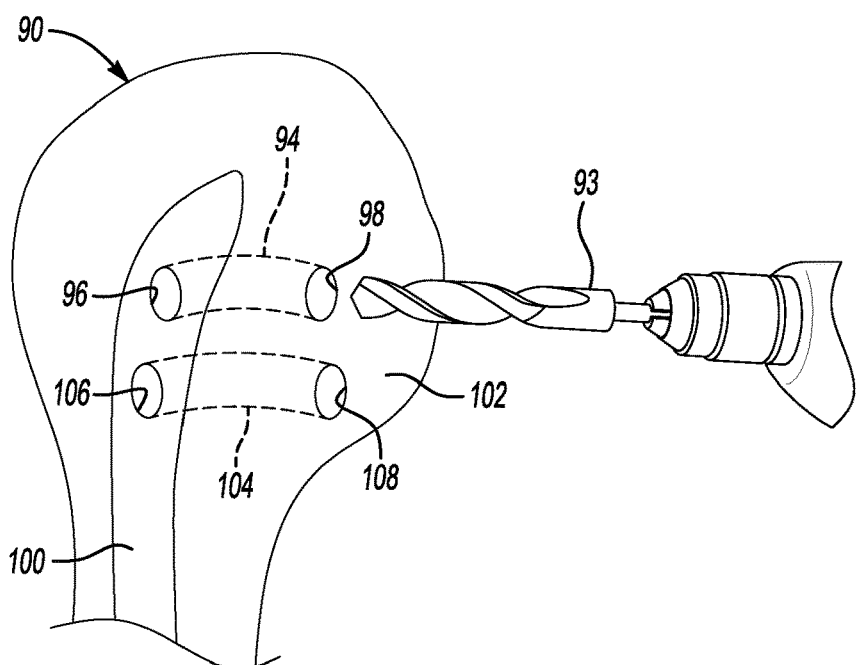
FIG. 4 shows the bone of FIG. 3 including tunnels established in the bone.

FIG. 3 illustrates an example humerus bone 90 and a subscapularis tendon (i.e., soft tissue) 92. As shown in FIG. 4, a surgical instrument 93, such as a drill, would be used by a physician to establish tunnels within the bone 90. In FIG. 4, a first tunnel 94 has openings or ends at 96 and 98. A first one of the ends 96 of the first tunnel 94 is located in the bicipital groove 100 of the humerus bone 90. The other end 98 of the first tunnel 94 is located on the medial side 102 of the bone 90. A second tunnel 104 has openings 106 and 108 at opposite ends of the second tunnel 104. The second tunnel is placed near the first tunnel with the end 106 also located in the bicipital groove 100.

One feature of the tunnel arrangement shown in FIG. 4 is that it allows for the buttons 22 and 64 of the surgical kit 20 to be received against the surface of the bone in the bicipital groove 100. This provides improved strength characteristics at the repair site because forces on the repair construct are borne by the portion of the bone including the bicipital groove 100, which is known to be a strong portion of the humerus. One aspect of a surgical technique designed according to an embodiment of this invention is that it facilitates using the strongest portion of the bone for bearing the loads associated with establishing the repair construct and maintaining soft tissue placement post-surgery.

Figure 5:
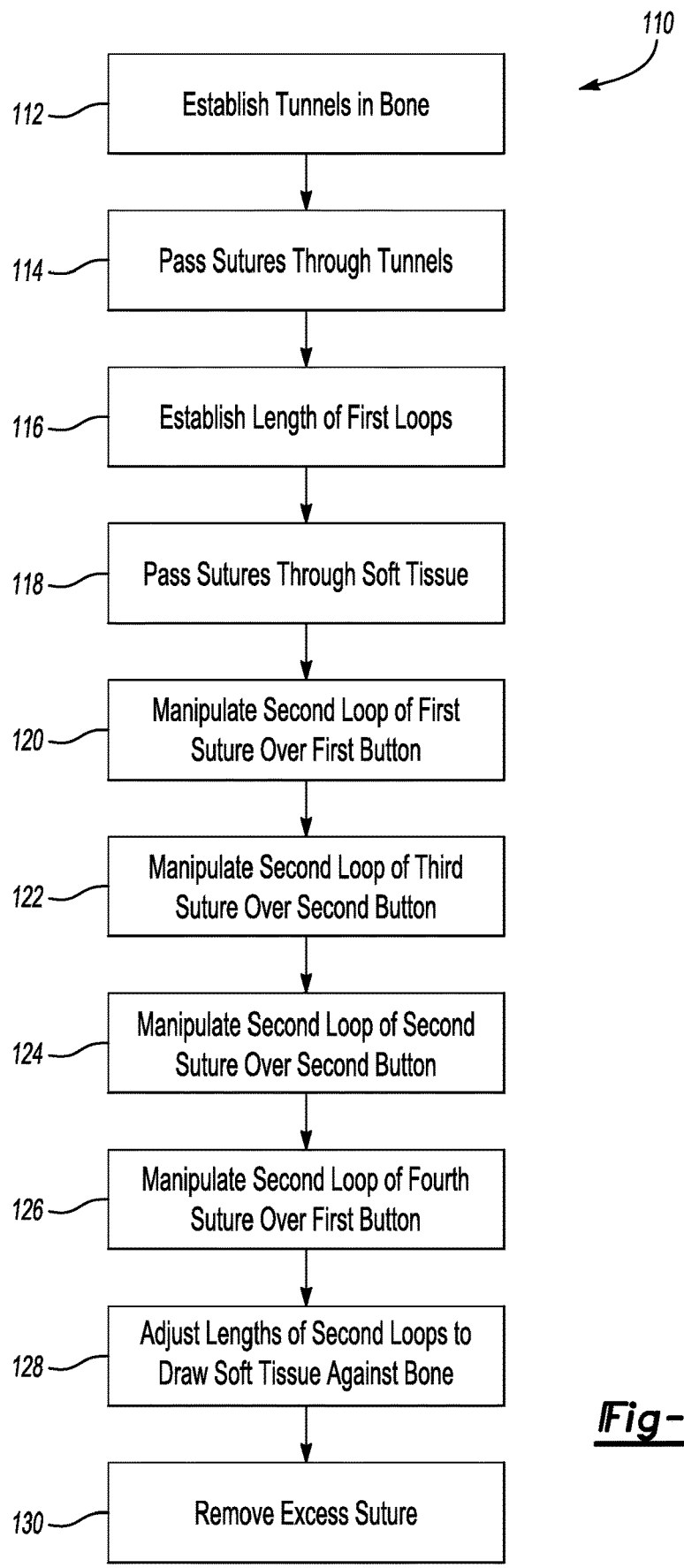
FIG. 5 is a flowchart diagram summarizing an example surgical technique designed according to an embodiment of this invention.
Figure 6:
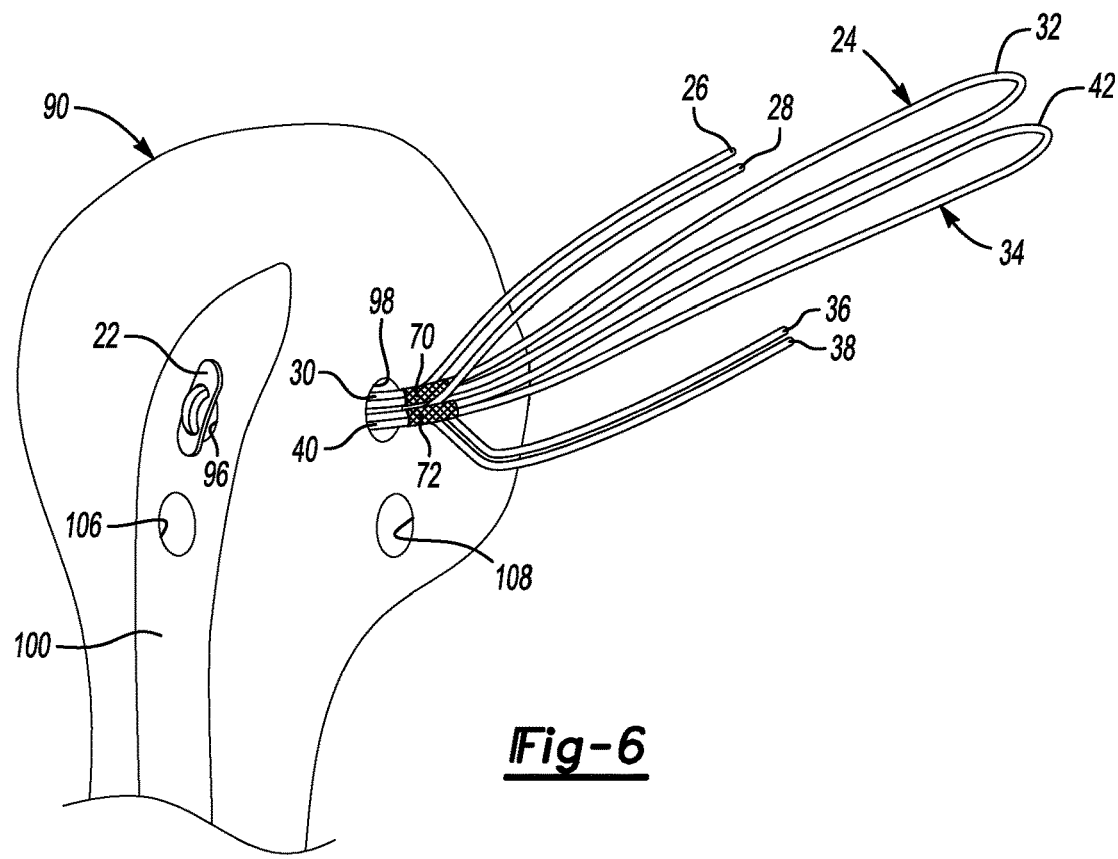
FIG. 6 illustrates a portion of an example surgical technique including placing sutures within one of the tunnels in the bone.

FIG. 5 includes a flowchart diagram 110 summarizing an example surgical technique. At 112, tunnels are established in bone, such as the tunnels 94 and 104 discussed above. At 114, sutures are passed through the tunnels. FIG. 6 illustrates the first suture 24 and second suture 34 passed through the first tunnel 94. As shown in FIG. 6, the first button 22 is situated near the first end 96 of the first tunnel 94 and the ends 26 and 28, the second loop 32 and a portion of the first loop 30 are situated near the second end 98 of the first tunnel 94.

At 116 in FIG. 5, the first loops are adjusted to have a length corresponding to or being the same as a length of the tunnel within which the first loop is received. By pulling on the end 26 of the first suture 24, a surgeon can shorten the length of the first loop 30 so that the length of that loop corresponds to the length of the first tunnel 94. In other words, a surgeon manipulates the suture to establish a length of the first loop 30 so that it is approximately equal to or the same as the length of the first tunnel 94. The length of the first loop 30 in this context refers to a distance from a portion of the loop threaded through the first button 22 to the opposite end of the first loop 30 near the securing member 70. In other words, the length of the first loop 30 in this context is based on a linear length of one side of the loop rather than the entire amount of suture establishing both sides of the loop.

In some example surgical techniques, the length of the first loop can be established to be the same as the length of the tunnel prior to, during or after the suture is situated within the tunnel. For convenience and accuracy, many embodiments include passing the suture through the tunnel first and then adjusting a length of the first loop to correspond to the length of the tunnel. With the adjusted length of the first loop, the entire first loop is situated inside the tunnel in many embodiments.

Figure 7:
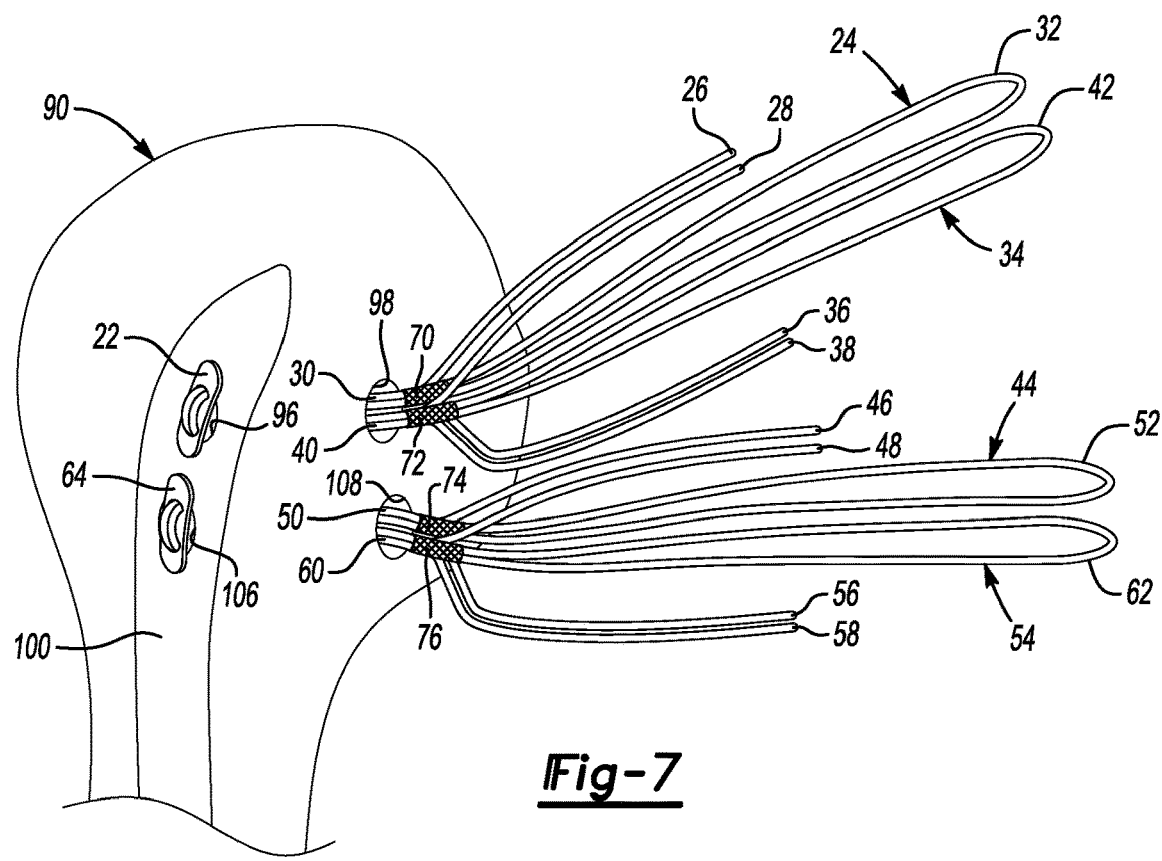
FIG. 7 illustrates another portion of the example surgical technique including placing sutures in the second tunnel in the bone.
Figure 8:
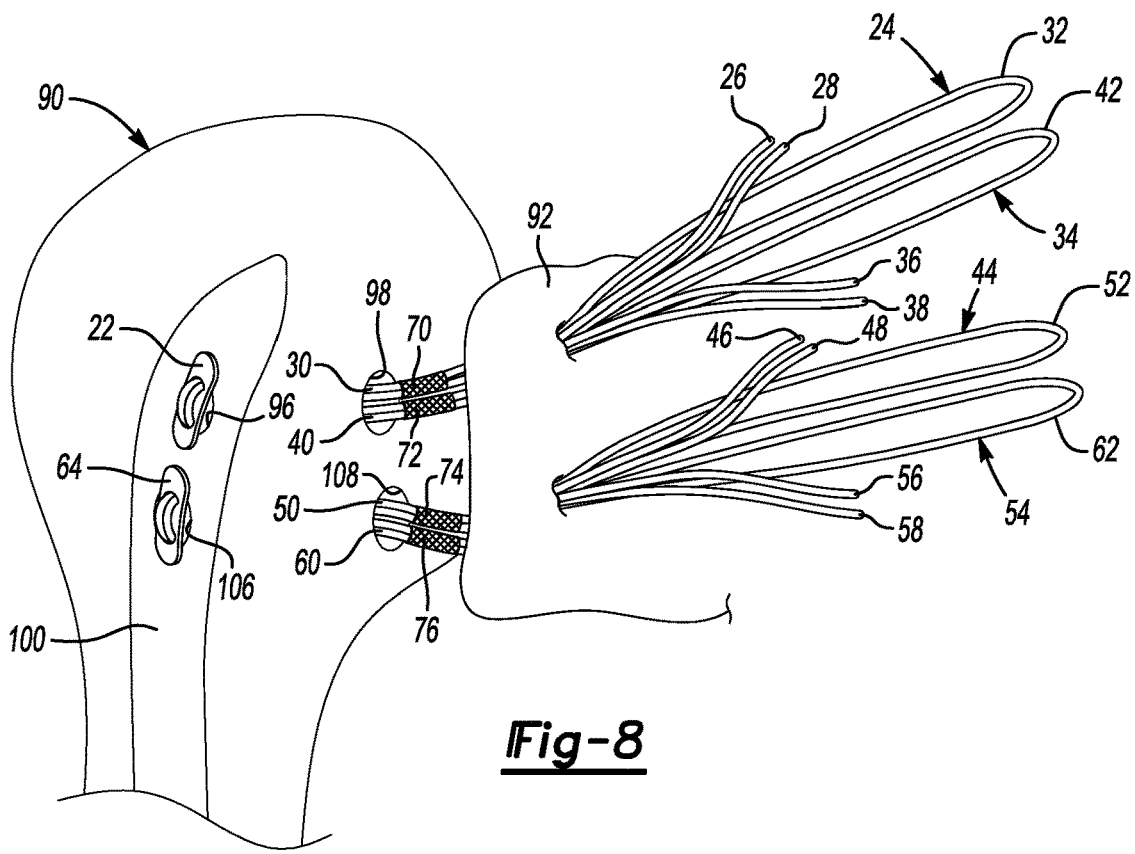
FIG. 8 illustrates another portion of the example surgical technique including passing at least a portion of the sutures through soft tissue.

FIG. 7 illustrates the third and fourth sutures 44 and 54 passed through the second tunnel 104.

Once all sutures are situated within the tunnels and the respective lengths of the first loops have been adjusted to correspond to the lengths of the corresponding tunnels, selected portions of the sutures are passed through the soft tissue 92. In this example, the ends of the sutures and the second loops of the sutures are passed through the soft tissue using an appropriate threading technique as can be accomplished using known surgical devices. This portion of the example procedure is in the flowchart of FIG. 5 at 118.

Figure 9:
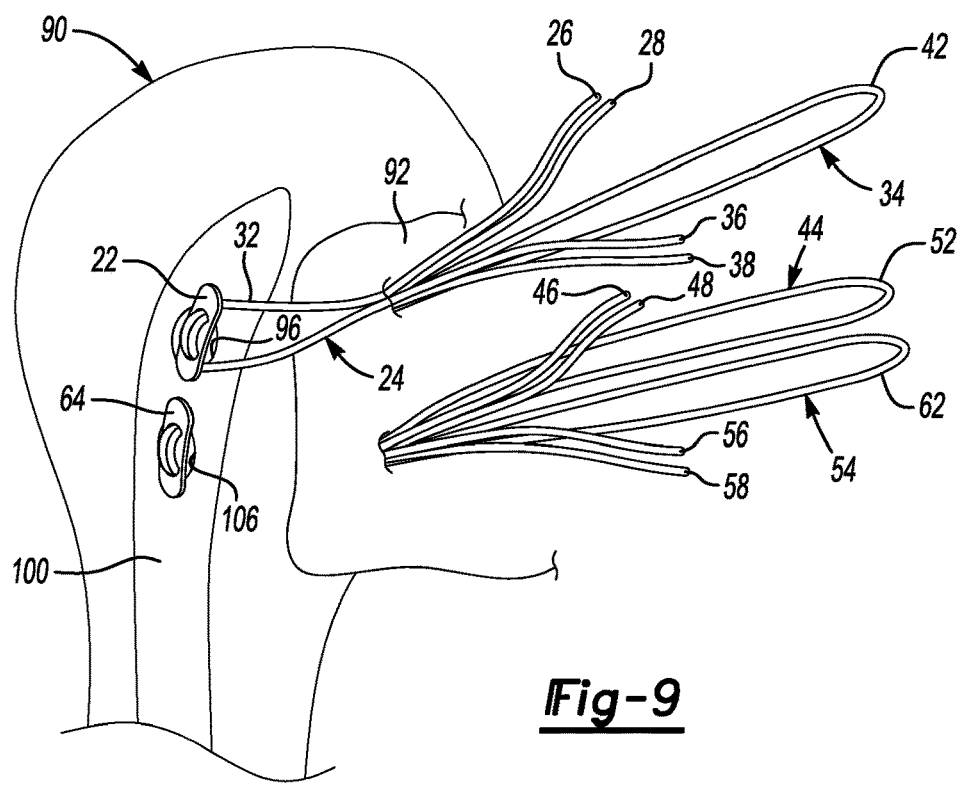
FIG. 9 illustrates another portion of the example surgical technique including manipulating a portion of one of the sutures over one of the buttons.
Figure 10:
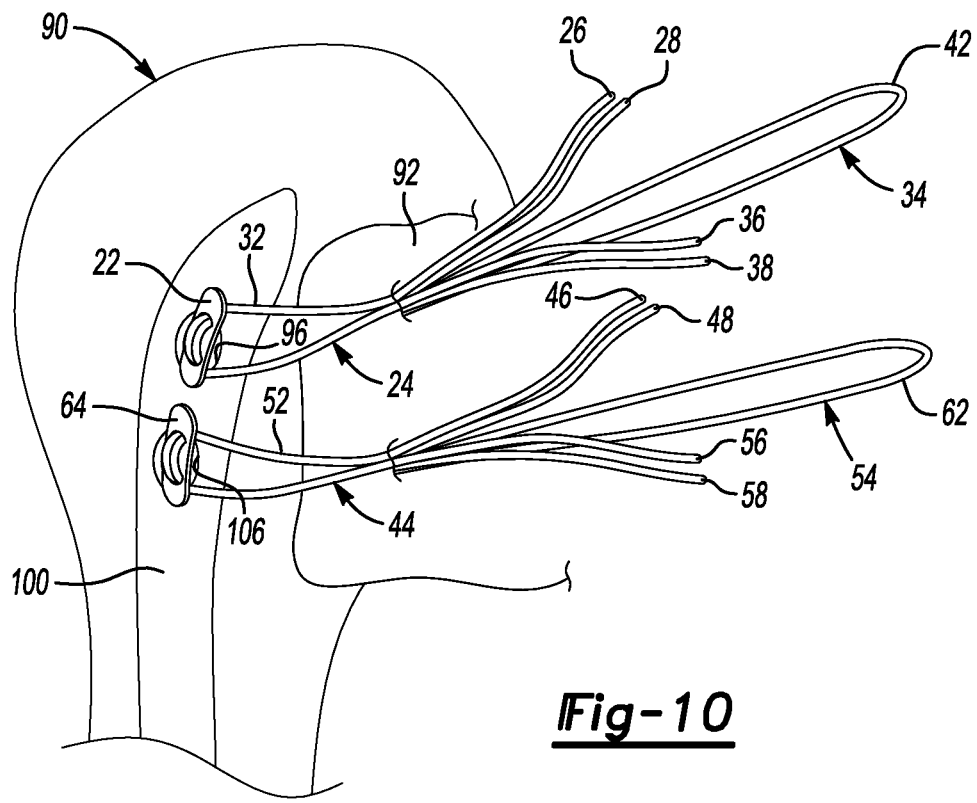
FIG. 10 illustrates another portion of the example surgical technique including manipulating a portion of another one of the sutures over another one of the buttons.

As shown at 120 in FIG. 5 and in FIG. 9, a surgeon manipulates the second loop 32 of the first suture 24 over the first button 22 so that a portion of the soft tissue 92 is positioned between the second loop 32 and the bone 90. As shown at 122 in FIG. 5 and in FIG. 10, manipulating the second loop 52 of the third suture 44 over the second button 64 positions the soft tissue 92 between the second loop 52 and the bone 90.

Figure 11:
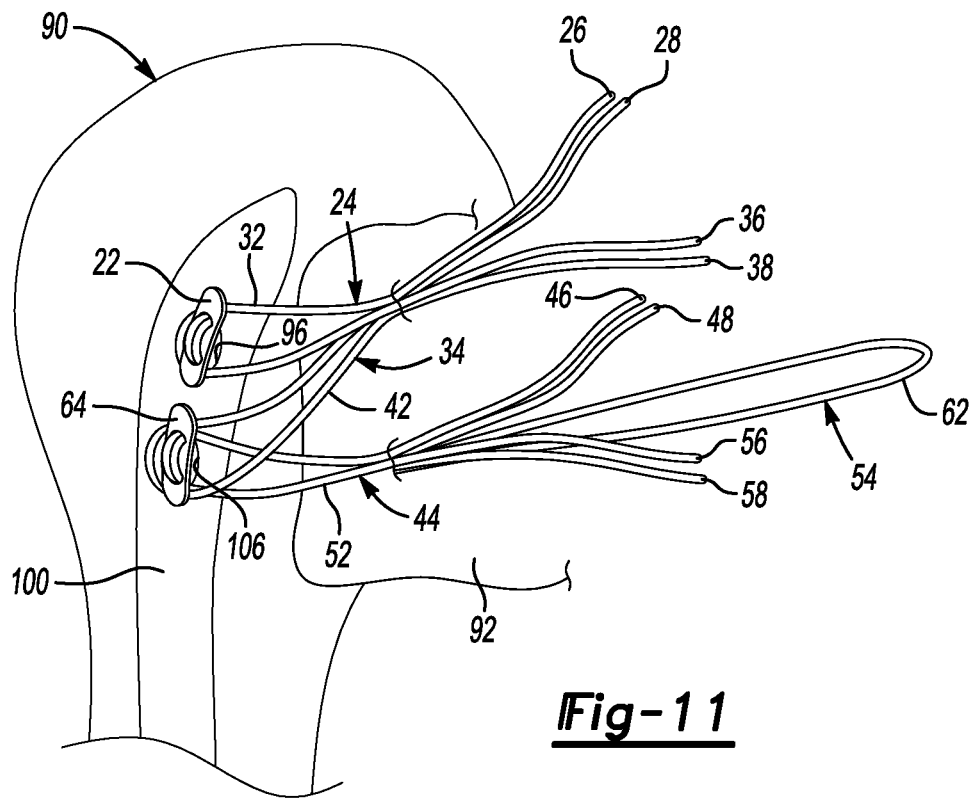
FIG. 11 illustrates another portion of the example surgical technique including manipulating another one of the sutures over one of the buttons.
Figure 12:
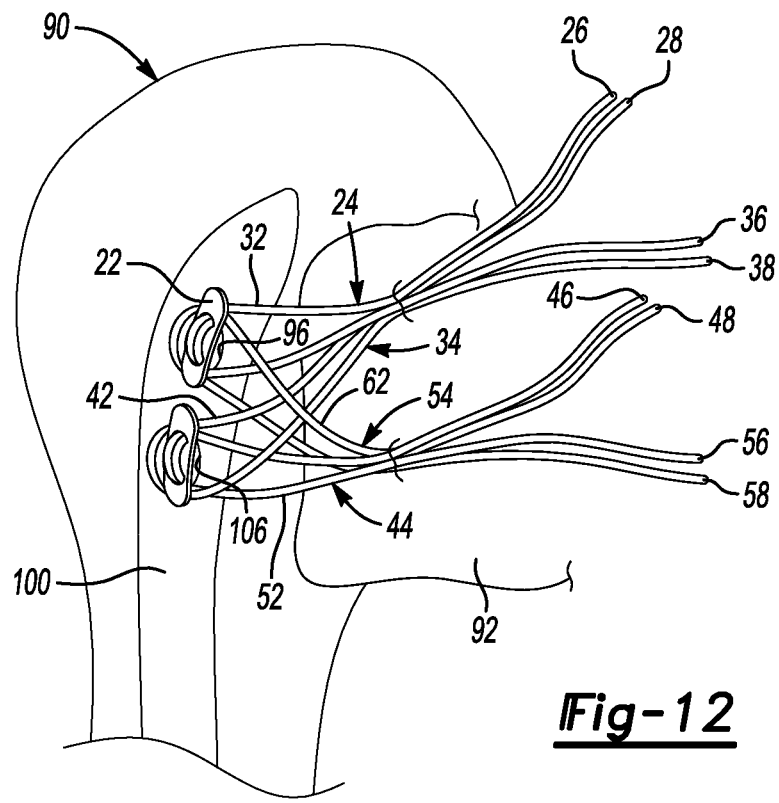
FIG. 12 illustrates another portion of the example surgical technique including manipulating a fourth one of the sutures over one of the buttons.

As shown in FIG. 5 at 124 and in FIG. 11, the second loop 42 of the second suture 34 is manipulated over the second button 64. At 126 in FIG. 5 and as shown in FIG. 12, the surgeon manipulates the second loop 62 of the fourth suture 54 over the first button 22. The illustrated arrangement of the second loops of suture establishes a mattress-style or cross-stitch repair construct with the sutures positioned over the soft tissue 92 so that the soft tissue is received between the sutures and the bone.

At 128 in FIG. 5, the lengths of the second loops are adjusted to draw the soft tissue 92 against the bone 90 with a desired tension or pressure at the repair site. The lengths of the second loops of the respective sutures may be adjusted after all second loops have been manipulated over the corresponding buttons or sequentially as each loop is manipulated over a corresponding button. Different surgeons may have difference preferences for the exact order of suture manipulation and loop length adjustment such that the order shown in FIG. 5 and described above is not necessarily limiting.

Figure 13:
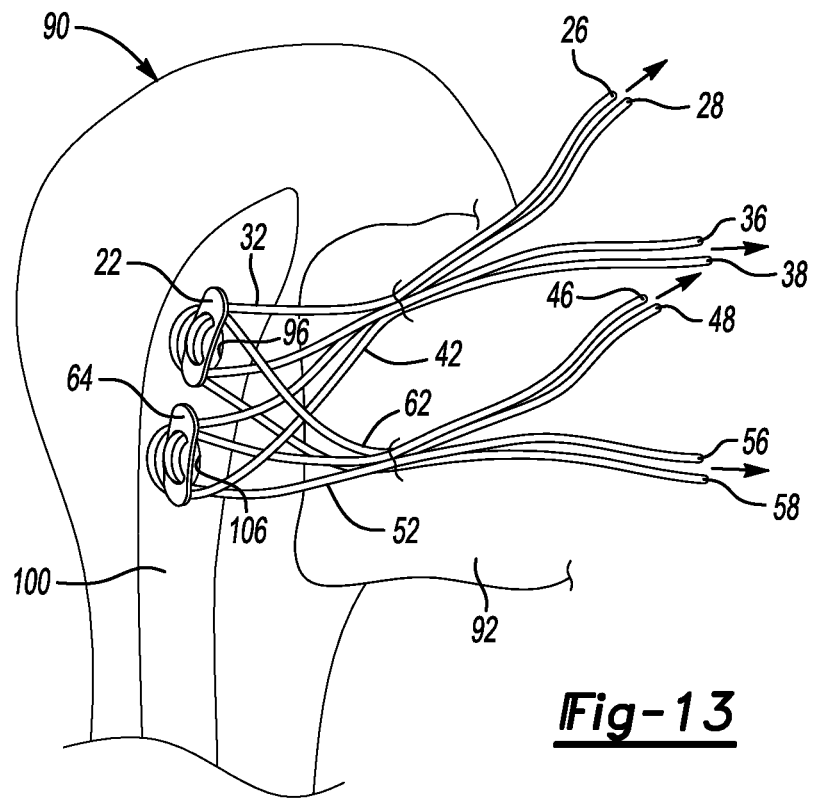
FIG. 13 illustrates another portion of the example surgical technique including adjusting portions of the sutures for holding the soft tissue against the bone without tying any knots in the sutures.

FIG. 13 schematically represents pulling on the second ends of the respective sutures to adjust the lengths of the second loops for securing the soft tissue 92 against the bone 90. The securing members 70-76 resist movement of the suture material relative to the securing member so that the length of the second loops remains fixed at a desired length without requiring any knot tying in any of the sutures. The manner in which the braid or securing members 70-76 are tensioned and received against the soft tissue in the example repair construct facilitates fixing the lengths of the respective second loops for maintaining a desired amount of pressure on the soft tissue 92 to hold the soft tissue 92 in the desired location to facilitate healing and reattachment to the bone 90.

Figure 14:
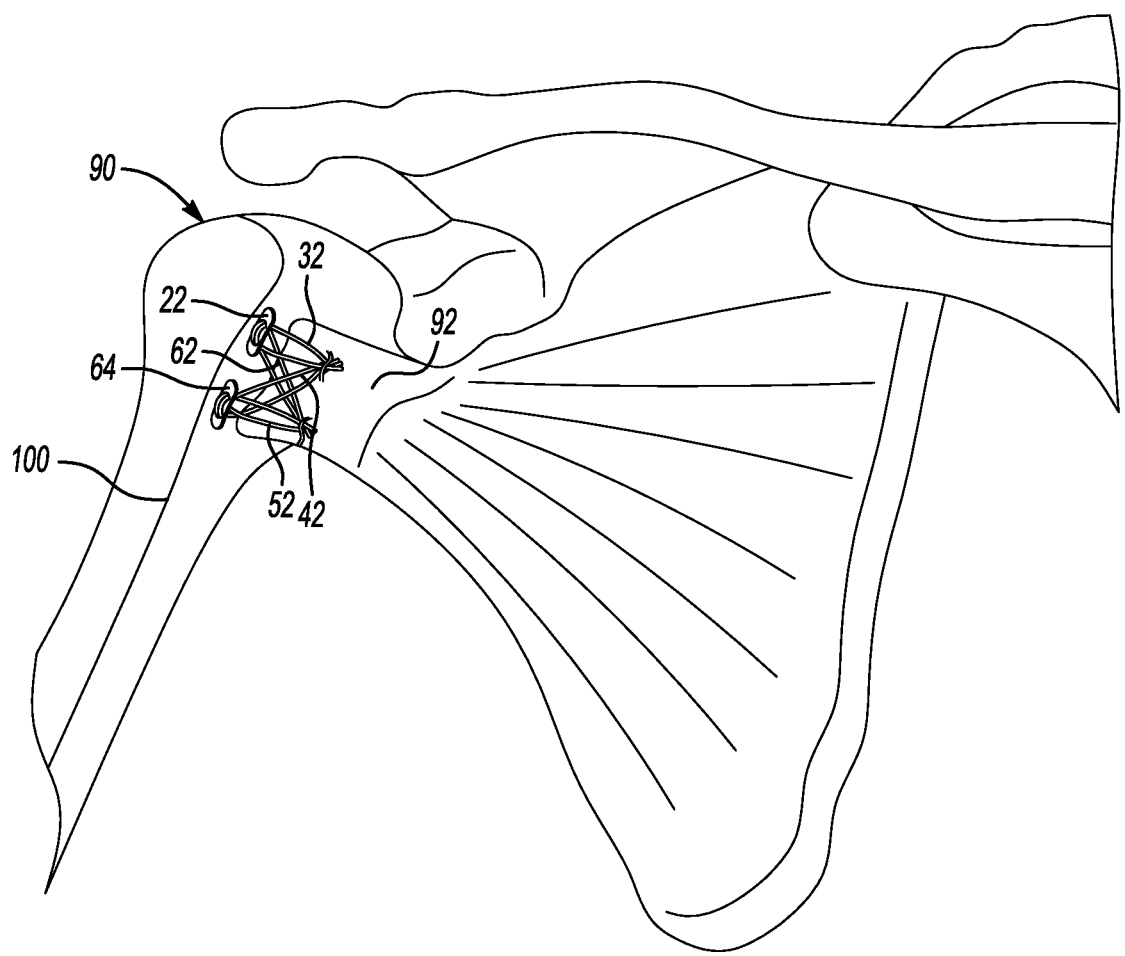
FIG. 14 illustrates an example result of the example surgical technique illustrated in FIGS. 6-13.

At 130 in FIG. 5 excess suture material is removed by cutting off the free ends extending beyond the length of the second loop. FIG. 14 illustrates an example result of a subscapularis tendon repair using the example technique described above.

The disclosed surgical kit and technique facilitate stable reattachment of soft tissue to bone for a variety of conditions and surgeries. A subscapularis tendon repair such as that described above may be done as part of a total shoulder or hemiarthroplasty surgery in which a portion of the humerus is repaired or replaced in a known manner. The example surgical kit and technique facilitate improved patient outcomes by avoiding the use of knots which otherwise may cause soft tissue irritation. Additionally, the example kit and technique reduce the complexity of the procedure by not requiring a surgeon to tie knots.

While two buttons and four sutures are included in the disclosed example, fewer buttons or fewer sutures may be used in some example embodiments. Depending on the particular tissue and anatomy involved, a surgeon may choose to use a single button or to use fewer than four sutures, for example.

The preceding description is exemplary rather than limiting in nature. Variations and modifications to the disclosed examples may become apparent to those skilled in the art that do not necessarily depart from the essence of this invention. The scope of legal protection given to this invention can only be determined by studying the following claims.

We claim:

1. A surgical method, comprising:
   establishing a tunnel in a bone;
   passing at least a portion of a suture through the tunnel, the suture having two ends and first and second loops between the two ends, the first loop including a button on the suture, the second loop having a portion disposed on one side of the tunnel and outside the bone, the button being on the other side of the tunnel after the passing;
   passing at least some of the portion of the second loop outside the bone through soft tissue;
   manipulating the portion of the second loop over the button into contact with the button to position a portion of the soft tissue between the second loop and the bone; and
   adjusting a length of the second loop to urge the portion of the soft tissue against the bone where the portion of the soft tissue is held by the suture without tying any knots in the suture.

2. The method of claim 1, comprising establishing a length of the first loop to be approximately the same as a length of the tunnel.

3. The method of claim 2, wherein establishing the length of the first loop comprises manipulating the suture to adjust the length of the first loop after passing at least the portion of the suture through the tunnel.

4. The method of claim 1, wherein
   the suture has at least one braid received over a portion of the suture; and
   respective portions of the suture are threaded through the at least one braid to establish the first and second loops.

5. The method of claim 4, wherein the at least one braid resists movement of the suture relative to the at least one braid after the length of the second loop is adjusted to urge the soft tissue against the bone to thereby maintain a length of the second loop that holds the soft tissue against the bone without tying any knots in the suture.

6. The method of claim 1, wherein the bone is a humerus having a bicipital groove and the button is received against the bicipital groove of the humerus.

7. The method of claim 1, comprising
   passing at least a portion of a second suture through the tunnel, the second suture having two second suture ends and first and second loops between the two second suture ends, the first loop of the second suture including the button on the second suture, the second loop of the second suture being on the one side of the tunnel after the passing;
   passing at least some of the second loop of the second suture through the soft tissue; and
   using the second suture to hold the portion of the soft tissue against the bone without tying any knots in the second suture.

8. The method of claim 7, comprising
   establishing a second tunnel in the bone;
   passing at least a portion of a third suture and a fourth suture through the second tunnel, each of the third and fourth sutures having two ends and first and second loops between the two ends, the first loop of each of the third and fourth sutures including a second button on the respective suture, the second loops of each of the third and fourth sutures being on one side of the second tunnel and the second button being on the other side of the second tunnel after the passing;
   passing at least some of the second loop of each of the third and fourth sutures through the soft tissue;

manipulating the second loop of the third suture over the second button with the portion of the soft tissue between the second loop of the third suture and the bone;

manipulating the second loop of the fourth suture over the button with the portion of the soft tissue between the second loop of the fourth suture and the bone;

manipulating the second loop of the second suture over the second button with the portion of the soft tissue between the second loop of the second suture and the bone; and adjusting a length of the second loop of each of the second, third and fourth sutures to urge the portion of the soft tissue against the bone where the portion of the soft tissue is held by the sutures without tying any knots in the sutures.

9. The method of claim 8, wherein each of the sutures has at least one respective braid received over a portion of the suture;

respective portions of the respective sutures are threaded through the respective at least one braid to establish the respective first and second loops; and each of the at least one braids resists movement of the respective suture relative to the respective at least one braid after the length of the respective second loop is adjusted to urge the soft tissue against the bone to thereby maintain a length of the respective second loop that holds the soft tissue against the bone without tying any knots.

10. The method of claim 8, wherein the second loop of the second suture crosses the second loop of the fourth suture.

11. The method of claim 8, wherein the bone is a humerus;

the button is received in a bicipital groove of the humerus; and the second button is received in the bicipital groove.

12. The method of claim 8, wherein the soft tissue comprises a subscapularis tendon.

13. The method of claim 8, comprising performing the method as part of a shoulder arthroplasty procedure.

14. The method of claim 8, comprising adjusting a length of the first loop of the second suture to be approximately the same as the length of the tunnel;

adjusting a length of the first loop of the third suture to be approximately the same as a length of the second tunnel; and adjusting a length of the first loop of the fourth suture to be approximately the same as the length of the second tunnel.

* * * * *